United States Patent [19] [11] 4,208,428
Kurono et al. [45] Jun. 17, 1980

[54] PROSTAGLANDIN ANALOGUES

[75] Inventors: Masayasu Kurono; Nobuyuki Hamanaka, both of Osaka; Shigeru Sakuyama, Nagaokakyo; Takeshi Chiba; Hisao Nakai, both of Takatsuki, all of Japan

[73] Assignee: Ono Pharmaceutical Co. Ltd., Osaka, Japan

[21] Appl. No.: 924,343

[22] Filed: Jul. 13, 1978

[30] Foreign Application Priority Data

Jul. 14, 1977 [JP] Japan .................................. 52-83558

[51] Int. Cl.² .................... C07C 177/00; A61K 31/19; A61K 31/215
[52] U.S. Cl. ............................. 424/305; 260/346.22; 260/456 P; 536/103; 542/426; 560/53.53; 560/118; 562/463; 562/465; 562/500; 424/308; 424/317
[58] Field of Search ....................... 560/118; 536/103; 562/500; 424/305, 317

[56] References Cited
U.S. PATENT DOCUMENTS 3,997,588 12/1976 Mueller ................................ 560/121
4,117,119 9/1978 Kurono et al. ....................... 424/180

Primary Examiner—Robert Gerstl
Attorney, Agent, or Firm—Albert H. Graddis

[57] ABSTRACT

The invention relates to prostaglandin analogues of the general formula:

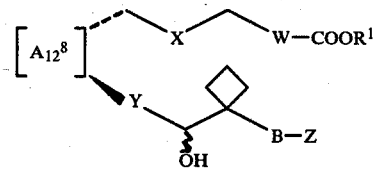

(wherein A represents a grouping of the formula:

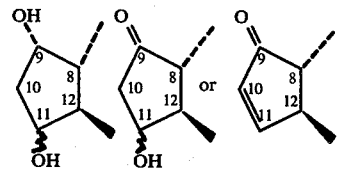

B represents an alkylene group containing from 1 to 7 carbon atoms or a group

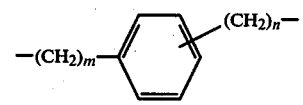

(wherein the group —$(CH_2)_n$— may be attached to the ortho, meta or para position of the phenyl ring and m and n, which may be the same or different, each represent an integer from 1 to 5 inclusive, the sum of the integers represented by m and n being from 2 to 6 inclusive), X represents ethylene or cis-vinylene, Y represents ethylene or trans-vinylene, W represents ethylene or trans-vinylene, Z represents a halogen atom, and $R^1$ represents a hydrogen atom or an alkyl group containing from 1 to 12 carbon atoms) and cyclodextrin clathrates of such acids and esters and, when $R^1$ represents a hydrogen atom, non-toxic salts thereof, which possess characteristic prostaglandin-like properties.

16 Claims, No Drawings

PROSTAGLANDIN ANALOGUES

This invention is concerned with new prostaglandin analogues.

Prostaglandins are derivatives of prostanoic acid which has the following formula:

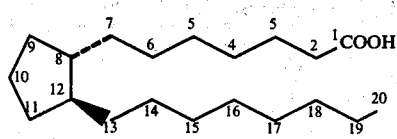

I

Various types of prostaglandins are known, the types depending inter alia on the structure and substituents on the alicyclic ring. For example, the alicyclic rings of prostaglandins F(PGF), E(PGE) and A(PGA) have the structures:

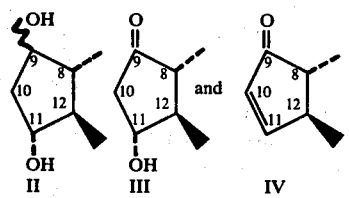

II     III     IV respectively. The dotted lines in the foregoing formulae and in other formulae throughout this specification denote, in accordance with generally accepted rules of nomenclature, that the attached grouping lies behind the general plane of the ring system, i.e. that the grouping is in α-configuration, the thickened lines denote that the grouping lies in front of the general plane of the system, i.e. that the grouping is in β-configuration, and the wavy line indicates that the grouping is in α-or β-configuration.

Such compounds are sub-classified according to the position of double bond(s) in the side chains(s) attached to the 8- and 12-positions of the alicyclic ring. Thus $PG_1$ compounds have a trans-double bond between $C_{13}-C_{14}(trans-\Delta^{13})$ and $PG_2$ compounds have a cis-double bond between $C_5-C_6$ and a trans-double bond between $C_{13}-C_{14}(cis-\Delta^5, trans-\Delta^{13})$. For example, prostaglandin $F_{1\alpha}$ ($PGF_{1\alpha}$) and prostaglandin $E_1$ ($PGE_1$) are characterised by the following structures V and VI.

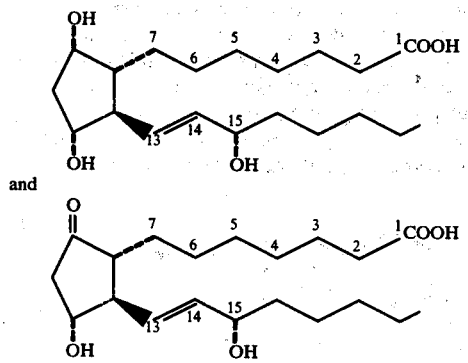

respectively. The structures of $PGF_{2\alpha}$ and $PGE_2$, as members of the $PG_2$ group, correspond to those of formulae V and VI respectively with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin-$F_{1\alpha}$ (dihydro-$PGF_{1\alpha}$) and dihydro-prostaglandin-$E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomenclature, as ω-homo-prostaglandin (methylene group added) or ω-nor-prostaglandins (methylene group eliminated), and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's and PGA's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGE's and PGF's have a stimulating effect on smooth muscle and increase the intestinal peristalsis; these actions indicate therapeutic utility on post-operative ileus and as purgatives. Furthermore, PGE's and PGF's may be used as oxytocics, as abortifacients in the first and second trimesters; in the post-labour abortion of the placenta, and as oral contraceptives because they regulate the sexual cycle of female mammals. PGE's and PGA's have vasodilator and diuretic activities. PGE's are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found after research and experimentation that by replacing the n-pentyl group attached to the carbon atom in the 15-position of the 'natural' prostaglandins by a group of the formula:

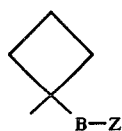

[wherein B represents a straight- or branched-chain alkylene group containing from 1 to 7 carbon atoms or a group

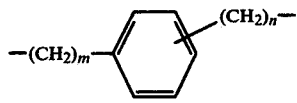

(wherein the group —$(CH_2)_n$— may be attached to the ortho, meta or para position of the phenyl ring and m and n, which may be the same or different, each represent an integer from 1 to 5 inclusive, the sum of the integers represented by m and n being from 2 to 6 inclusive), preferably a straight- or branched-chain alkylene group containing from 1 to 7 carbon atoms, more preferably the tetramethylene group, and Z represents a halogen atom (i.e. fluorine, chlorine, bromine or iodine atom)], new prostaglandin analogues are obtained which possess the pharmacological properties of the 'natural' prostaglandins and are, in some aspects of their activities, an improvement, for example possessing an enhanced strength of activity and/or a prolonged duration of activity.

The present invention accordingly provides the new prostaglandin analogues of the general formula:

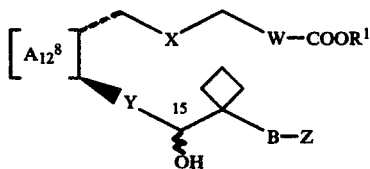

[wherein A represents a grouping of formula IV as indicated hereinbefore or a grouping of the formula:

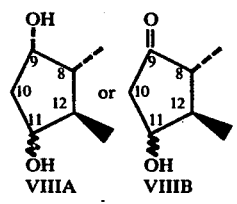

X represents ethylene (i.e. —$CH_2$—$CH_2$—) or cis-vinylene

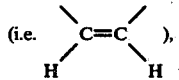

Y represents ethylene or trans-vinylene

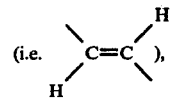

W represents ethylene or trans-vinylene, $R^1$ represents a hydrogen atom or a straight- or branched-chain alkyl group containing from 1 to 12 carbon atoms and B and Z are as hereinbefore defined] and cyclodextrin clathrates of such acids and esters and, when $R^1$ represents a hydrogen atom, non-toxic (e.g. sodium) salts thereof. Preferably the hydroxy group attached to the C-15 carbon atom of formula VII is in α-configuration; particularly preferred are those compounds wherein the hydroxy group depicted in formulae VIIIA and VIIIB in α- or β-configuration is attached to the 11-position carbon atom in α-configuration.

The present invention is concerned with all compounds of general formula VII in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VII have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carriers a hydroxy group on the carbon atom in position 11 (i.e. when the ring is that of formula VIIIB) or hydroxy groups in positions 9 and 11 (i.e. when the ring is that of formula VIIIA) and other centres of chirality may occur when B is a branched-chain alkyl group. The presence of chirality leads, as is well known, to the existence of isomerism. However, the compounds of general formula VII all have such a configuration that the side-chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans configuration and have a hydroxy group as depicted in the 15-position are to be considered within the scope of formula VII.

According to a feature of the present invention, the prostaglandin analogues of general formula VII, wherein A represents a grouping of formula VIIIA or VIIIB, $R^1$ represents a hydrogen atom or a straight- or branched-chain alkyl group containing from 1 to 4 carbon atoms, and the other symbols are as hereinbefore defined, i.e. compounds of the general formula:

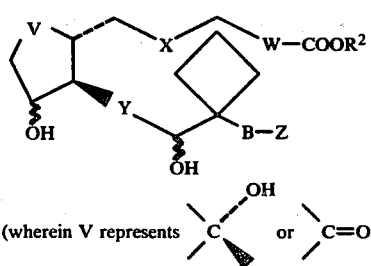

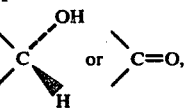

$R^2$ represents a hydrogen atom or a straight- or branched-chain alkyl group containing from 1 to 4 carbon atoms, and the other symbols are as hereinbefore defined) are prepared by halogenation of a compound of the general formula:

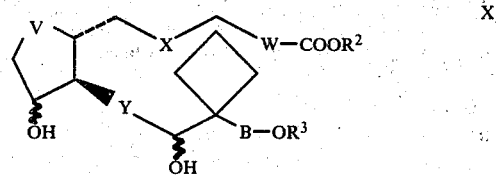
X (wherein $R^3$ represents an arylsulphonyl group, preferably a p-toluenesulphonyl or benzenesulphonyl group, and the other symbols are as hereinbefore defined) by methods known per se to convert the group $OR^3$ to a halogen atom. The halogenation may be suitably carried out, for example, with a halogenating reagent (e.g. potassium fluoride, lithium chloride, lithium bromide or lithium iodide) in N,N-dimethylformamide at room temperature. By the term 'methods known per se' as used in this specification is meant methods heretofore used or described in the chemical literature.

Compounds of general formula X may be prepared from compounds of the general formula:

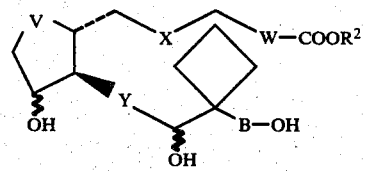
XI (wherein the various symbols are as hereinbefore defined) by sulphonylation with an arylsulphonyl chloride, e.g. p-toluenesulphonyl chloride or benzenesulphonyl chloride, in an inert organic solvent, e.g. methylene chloride, in the presence of a base, e.g. pyridine or a tertiary amine, at a temperature ranging from 0° C. to ambient temperature.

Compounds of general formula XI are prepared by the process which comprises hydrolyzing to hydroxy groups the groups $OR^4$ of a compound of the general formula:

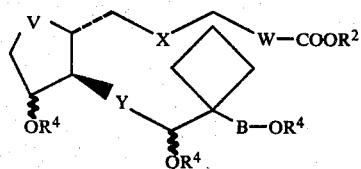
XII wherein $R^4$ represents a 2-tetrahydropyranyl or 2-tetrahydrofuranyl group each such group being unsubstituted or substituted by at least one alkyl group, or represents a 1-ethoxyethyl group, and the other symbols are as hereinbefore defined.

The groups $OR^4$ of the compounds of general formula XII may be converted to hydroxy groups by mild hydrolysis with an aqueous solution of an organic acid, e.g. acetic acid or oxalic acid, in the presence of a water-miscible organic solvent, e.g. tetrahydrofuran or an alkanol containing from 1 to 4 carbon atoms, e.g. methanol. The hydrolysis may be carried out at a temperature ranging from ambient to 70° C. (preferably at a temperature below 45° C.) with an acid mixture, e.g. a mixture of acetic acid, water and tetrahydrofuran.

According to a feature of the invention the PGE compounds of general formula IX, i.e. those compounds wherein V represents $>C=O$, may be converted to the corresponding PGA compounds of the general formula:

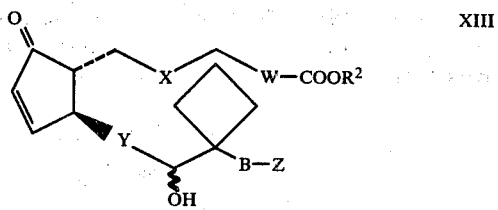
XIII (wherein the various symbols are as hereinbefore defined) by subjecting the PGE compounds to dehydration by methods known per se, e.g. using an aqueous solution of an organic or inorganic acid having a higher concentration than that employed for hydrolyzing the groups $OR^4$ of compounds of general formula XII, e.g. 1 N hydrochloric acid or acetic acid, and heating at a temperature of 30° to 60° C.

Compounds of general formula XII, wherein V represents $>C=O$, and the other symbols are as hereinbefore defined, i.e. compounds of the general formula:

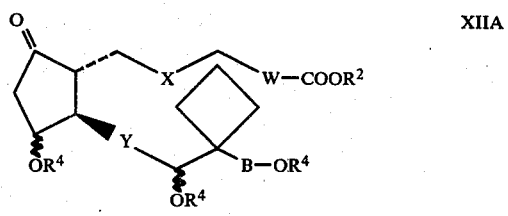
XIIA (wherein the various symbols are as hereinbefore defined) may be prepared from compounds of general formula XII, wherein V represents

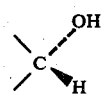

and the other symbols are as hereinbefore defined, by methods known per se for the conversion of a hydroxy group in the 9-position of a prostaglandin compound to an oxo group, for example by means of a chromic acid solution (obtained from chromium trioxide, manganese sulphate and sulphuric acid in water), Jones' reagent or a dimethylsulphide-N-chlorosuccinimide complex.

Compounds of general formula XII, wherein V represents

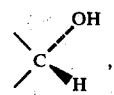

and the other symbols are as hereinbefore defined, i.e. compounds of the general formula:

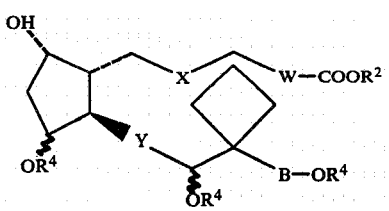

XIIB (wherein the various symbols are as hereinbefore defined), may be prepared by the series of reactions depicted schematically below in Scheme A:

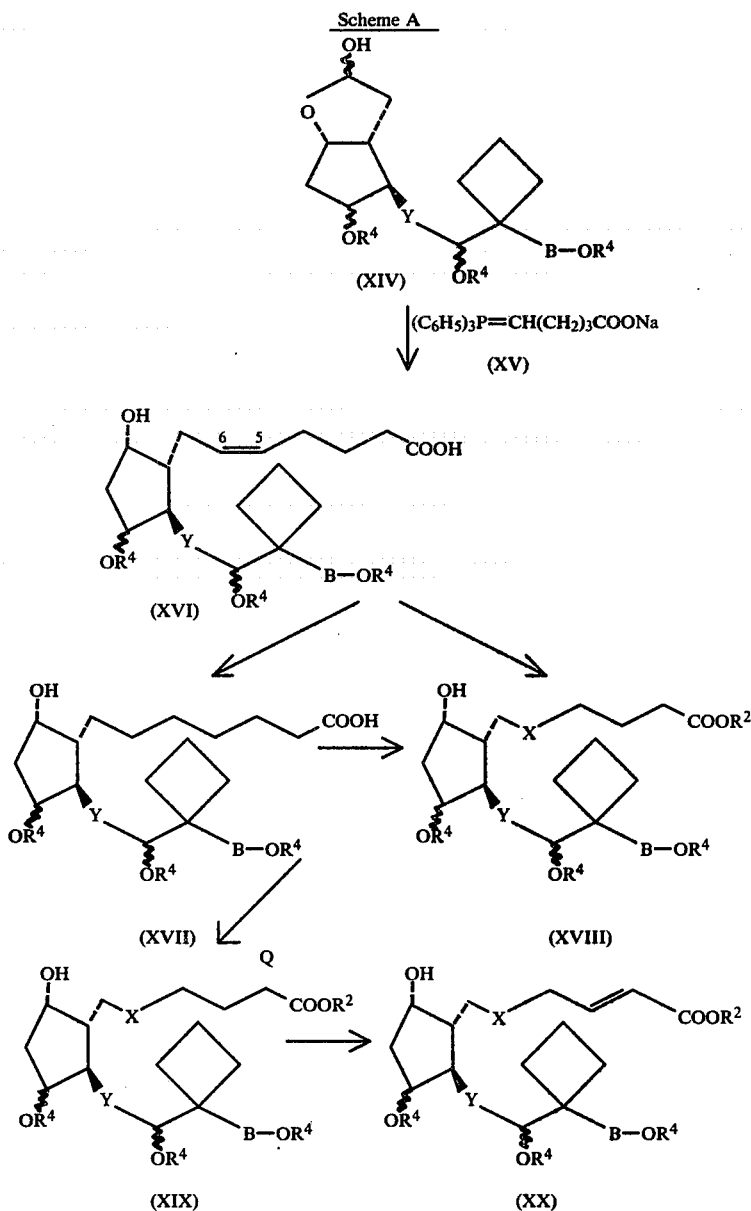

wherein Q represents the group —SeC$_6$H$_5$ or —SR$^5$, wherein R$^5$ represents an alkyl group containing from 1 to 4 carbon atoms or a phenyl group, and the other symbols are as hereinbefore defined.

The reaction between the bicyclooctane compounds of the general formula XIV and (4-carboxybutylidene)-triphenylphosphorane of the formula XV [obtained by the reaction of sodium methylsulphinylmethylide with (4-carboxybutyl)triphenylphosphonium bromide, cf. E. J. Corey et al., J. Amer. Chem. Soc., 91, 5675 (1969)] is carried out under the normal conditions utilized for effecting the Wittig reaction, e.g. in an inert organic solvent at ambient temperature. The reaction is preferably carried out in dimethyl sulphoxide because the phosphorane compound is practically insoluble in other solvents, e.g. tetrahydrofuran, and because a cis-double bond must be formed stereospecifically in the Wittig reaction. For the better performance of the Wittig reaction two to four molecular equivalents of the phosphorane compound are required for each mole of the bicyclooctane reactant. The reaction is generally effected at ambient temperature (e.g. about 25° C.) and is usually complete after about 1.5 to four hours. The acid product of formula XVI may be extracted from the reaction mixture by conventional procedures.

Compounds of general formula XVI may, if desired, be reduced to give compounds of general formula XVII. Suitably, the reduction may be effected by catalytic hydrogenation in the presence of a hydrogenation catalyst and in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter. When it is desired to obtain compounds of general formula XVII, wherein Y represents trans-vinylene, the hydrogenation catalyst may be, for example, palladium on charcoal, palladium black or a nickel catalyst, the hydrogenation being monitored to avoid any reduction of the trans-vinylene group Y in the starting material of general formula XVI. When it is desired to obtain compounds of general formula XVII, wherein Y represents ethylene, by reduction of the $C_5$-$C_6$ cis-vinylene group and a trans-vinylene group Y of compounds of general formula XVI, more active catalysts such as platinum black are required, and the hydrogenation is carried out until two times the molar quantity of hydrogen has been consumed.

The compounds of general formula XVIII, wherein $R^2$ represents a straight- or branched-chain alkyl group containing from 1 to 4 carbon atoms, are prepared by esterification of the corresponding acids of general formula XVI or XVII with (i) diazoalkane compounds, e.g. diazomethane, (ii) alcohols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our British Pat. Nos. 1,362,956 and 1,364,125).

The compounds of general formula XVIII may be converted to the compounds of general formula XX via compounds of general formula XIX by the following procedure.

Compounds of general formula:

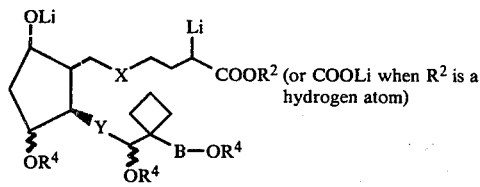

(wherein the various symbols are as hereinbefore defined) may be prepared from the compounds of general formula XVIII by reaction with a lithium salt of a secondary amine (e.g. lithium diisopropylamide), (1) when $R^2$ represents a hydrogen atom, in tetrahydrofuran in the presence of hexamethylphosphotriamide at 0° C., or (2) when $R^2$ represents an alkyl group, in tetrahydrofuran at a low temperature, e.g. at $-78°$ C.

Compounds of general formula XIX may be prepared from compounds of general formula XXI by reaction with benzeneselenenyl bromide (i.e. $C_6H_5SeBr$) or diphenyldiselenide (i.e. $C_6H_5Se-SeC_6H_5$) or a dialkyldisulphide or diphenyldisulphide of the formula $R^5-S-S-R^5$ (wherein $R^5$ is as hereinbefore defined) in an inert organic solvent, e.g. tetrahydrofuran, hexamethylphosphotriamide, diethyl ether, n-hexane or n-pentane or a mixture of two or more of them, at a low temperature, for example when $R^2$ is an alkyl group, at $-78°$ C., or, when $R^2$ is a hydrogen atom, at 0° C., followed by hydrolysis of the resulting organolithium compound, for example by treatment with an aqueous solution of ammonium chloride to give compounds of general formula XIX.

Compounds of general formula XIX, wherein Q represents the group $-SeC_6H_5$, may be converted to compounds of general formula XX by reaction (1) with hydrogen peroxide in a mixture of ethyl acetate and tetrahydrofuran or methanol, preferably in the presence of sodium bicarbonate at a temperature below 30° C., or (2) with sodium periodate in a mixture of water and a lower alkanol, e.g. methanol or ethanol, preferably in the presence of sodium bicarbonate at a temperature below 30° C.

Compounds of general formula XIX, wherein Q represents the group -$SR^5$ ($R^5$ being as hereinbefore defined), may be converted to compounds of the general formula:

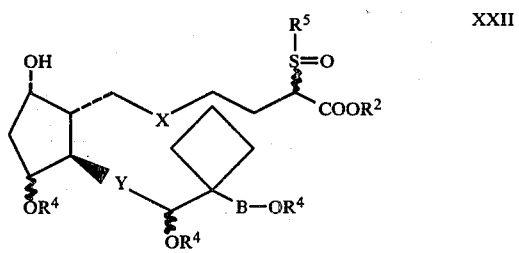

(wherein the various symbols are as hereinbefore defined) by means heretofore mentioned for the conversion of compounds of general formula XIX, wherein Q represents the group —$SeC_6H_5$, to those of general formula XX.

Further treatment is required to convert compounds of general formula XXII to compounds of general formula XX. The conversion may be effected by treatment (1) when $R^5$ represents an alkyl group, in toluene, preferably in the presence of a small amount of calcium carbonate, at a temperature of 100° to 120° C., or (2) when $R^5$ represents a phenyl group, in carbon tetrachloride, preferably in the presence of a small amount of calcium carbonate, at a temperature of about 50° C.

The bicyclooctane derivatives of general formula XIV are new compounds and may be prepared by the series of reactions depicted schematically below in Scheme B:

Scheme B
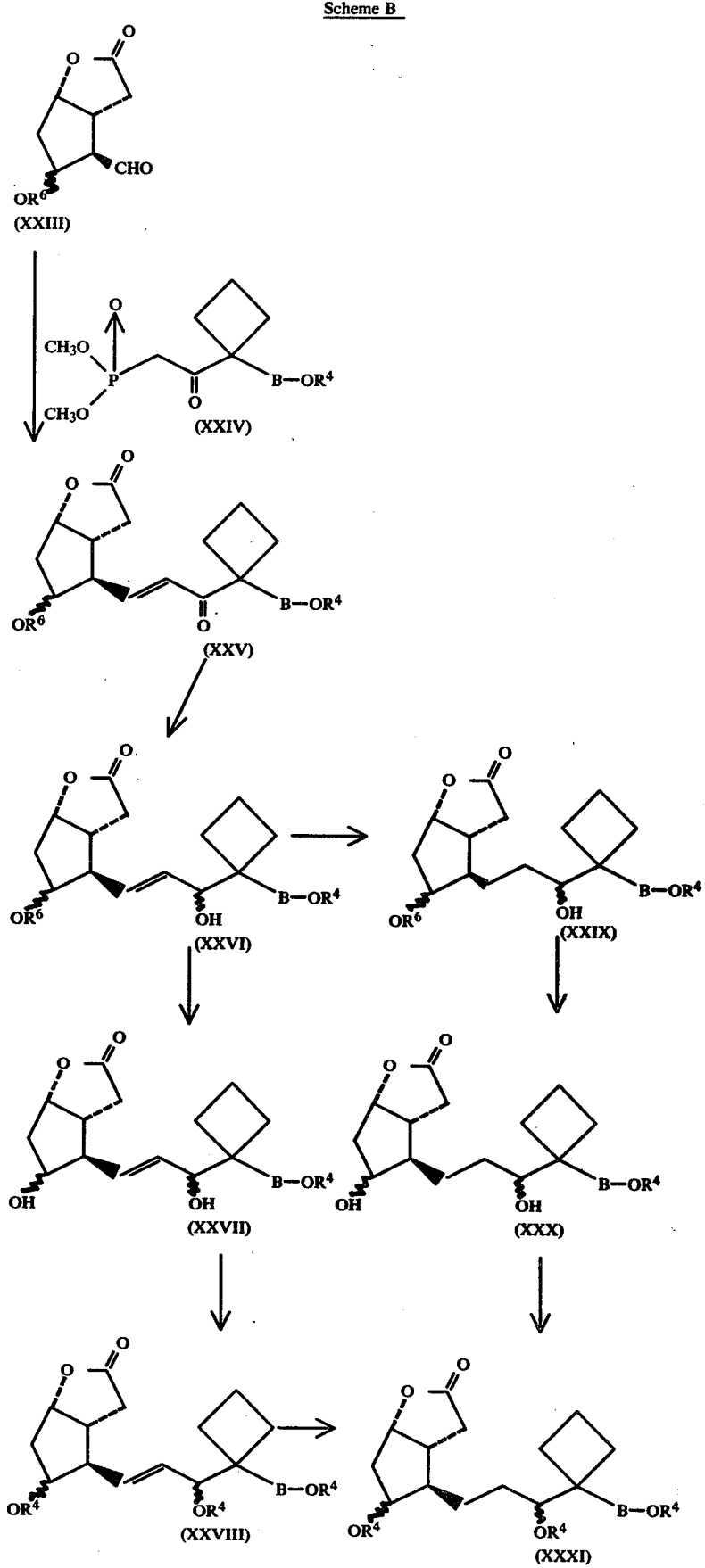

Scheme B

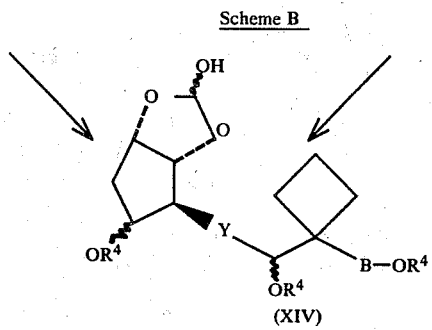

(XIV)

wherein R⁶ represents an acetyl group or a p-phenylbenzoyl group, and the other symbols are as hereinbefore defined.

The phosphonates of general formula XXIV are initially converted to corresponding ylides by reaction with sodium hydride in a polar aprotic solvent, for example tetrahydrofuran or 1,2-dimethoxyethane. The alicyclic aldehyde compounds of general formula XXIII are added to the ylide and the ensuing Wittig reaction carried out to obtain the enone compounds of general formula XXV. These compounds are reduced with zinc borohydride or sodium borohydride in an inert organic solvent, e.g. 1,2-dimethoxyethane, methanol or tetrahydrofuran, to give compounds of general formula XXVI. The α- and β-hydroxy isomers obtained by the reduction may be separated at this stage by column chromatography or the separation of α- and β-hydroxy isomers may be deferred, separation being carried out on the mixture of corresponding isomers of general formula VII. Optionally, the bicyclooctane compounds of general formula XXVI may be catalytically hydrogenated to corresponding compounds of general formula XXIX by means heretofore mentioned for the hydrogenation of compounds of general formula XVI to those of general formula XVII. Hydrolysis of compounds of general formula XXVI or XXIX, with, for example, an equimolar amount of anhydrous potassium carbonate in methanol at ambient temperature, gives the diols of general formula XXVII or XXX respectively, which are then etherified to introduce groups R⁴ (R⁴ being as hereinbefore defined), for example by reaction with a 2,3-dihydropyran, a 2,3-dihydrofuran or vinyl ethyl ether in an inert organic solvent, e.g. methylene chloride, at ambient temperature using p-toluenesulphonic acid as a catalyst, to give ethers of general formula XXVIII or XXXI. Optionally the bicyclooctane compounds of general formula XXVIII may be catalytically hydrogenated to corresponding compounds of general formula XXXI by means heretofore mentioned for the hydrogenation of compounds of general formula XVI to those of general formula XVII. Reduction of the ethers of general formula XXVIII or XXXI is then effected with diisobutylaluminium hydride in toluene at a low temperature, e.g. −60° C., to give the bicyclooctane derivatives of general formula XIV.

The aldehyde compounds of general formula XXIII are known. When R⁶ represents the acetyl group, the racemic form is described in J. Amer. Chem. Soc., 91, 5675 (1969) and the natural form is described in J. Amer. Chem. Soc., 92, 397 (1970). When R⁶ represents the p-phenylbenzoyl group, the natural form is described in J. Amer. Chem. Soc., 93, 1491 (1971).

The phosphonates of general formula XXIV may be prepared by the series of reactions depicted schematically below in Scheme C:

Scheme C

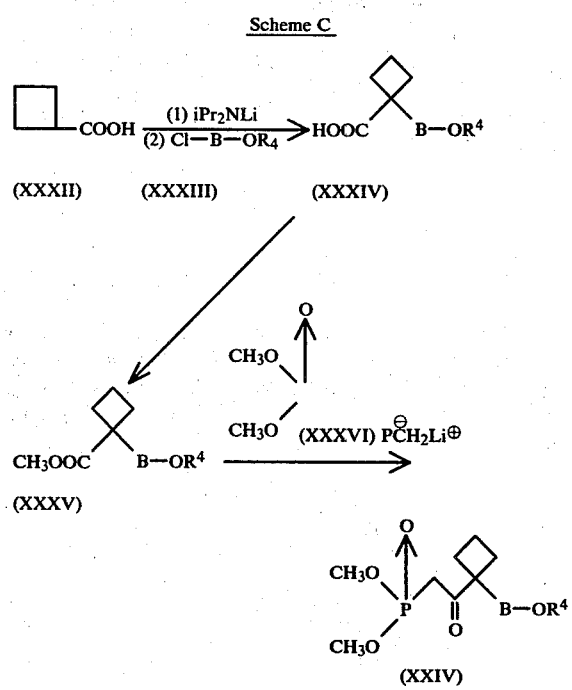

wherein iPr represents the isopropyl group, and the other symbols are as hereinbefore defined.

The cyclobutanecarboxylic acid of formula XXXII, used as a starting material in these reactions, is a known compound and is described in Org. Syn., Coll, Vol. III, 213.

Treatment of the cyclobutanecarboxylic acid with more than two molecular equivalents of lithium diisopropylamide in an aprotic solvent, e.g. tetrahydrofuran, followed by treatment of the product with a compound of the general formula XXXIII (wherein R⁴ is as hereinbefore defined) gives the 1-substituted-cyclobutanecarboxylic acids of general formula XXXIV which are converted to the methyl esters of general formula XXXV by methods known per se. The esters of general formula XXXV are treated with more than two molecular equivalents of the lithio derivative of formula XXXVI in an aprotic solvent, e.g. tetrahydrofuran, at a temperature at or below 0° C., to give the desired phosphonates of general formula XXIV.

According to a further feature of the present invention prostaglandin analogues of general formula VII, wherein A represents a grouping of formula VIIIA or VIIIB, $R^1$ represents a hydrogen atom or a straight- or branched-chain alkyl group containing from 1 to 4 carbon atoms, Z represents a fluorine atom and the other symbols are as hereinbefore defined, may be prepared by hydrolyzing to hydroxy groups the groups $OR^4$ of a compound of the general formula:

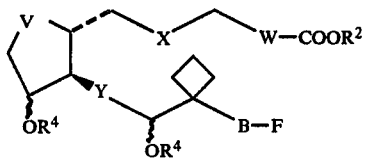

XIIC (wherein the various symbols are as hereinbefore defined) by mild hydrolysis as hereinbefore described for the conversion of compounds of general formula XII to compounds of general formula XI. Preferably $R^4$ in general formula XIIC represents a 2-tetrahydropyranyl group.

Compounds of general formula XIIC, wherein V represents

and the other symbols are as hereinbefore defined, may be prepared by the series of reactions hereinbefore depicted in Scheme A, but replacing the starting material of general formula XIV by a compound of the general formula:

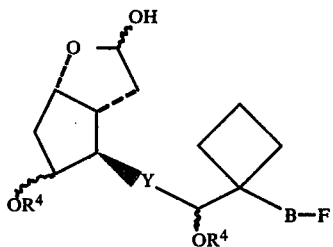

XXXVII (wherein the various symbols are as hereinbefore defined) to obtain compounds of the general formula:

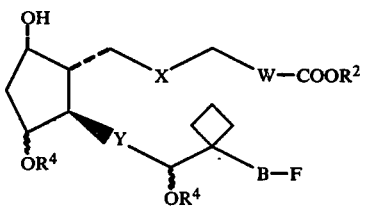

XIID wherein the various symbols are as hereinbefore defined.

Compounds of general formula XIID may be converted to compounds of general formula XIIC, wherein V represents $>C=O$ and the other symbols are as hereinbefore defined, i.e. compounds of the general formula:

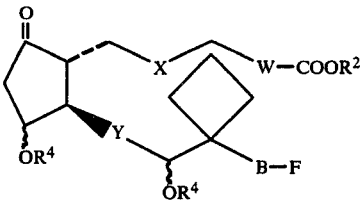

XIIE (wherein the various symbols are as hereinbefore defined) by means heretofore mentioned for the conversion of compounds of general formula XIIB to compounds of general formula XIIA.

Compounds of general formula XXXVII may be prepared by the series of reactions hereinbefore depicted in Scheme B, but replacing the compounds of general formula XXIV by compounds of the general formula:

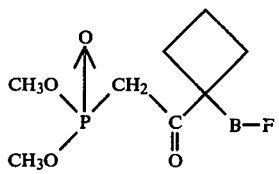

XXXVIII wherein B is as hereinbefore defined.

Compounds of general formula XXXVIII may be prepared by the series of reactions depicted schematically below in Scheme D:

Scheme D

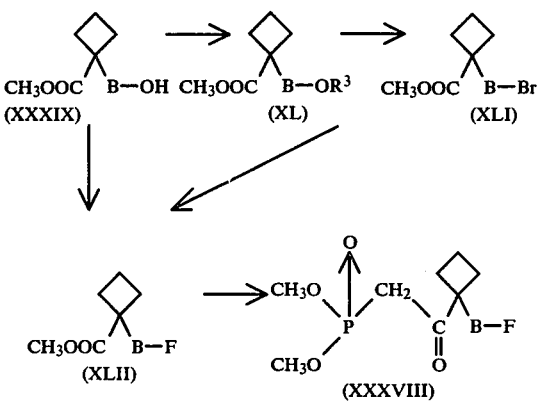

wherein the various symbols are as hereinbefore defined.

The compounds of general formula XXXIX are prepared from compounds of general formula XXXV by hydrolysis by methods known per se. Compounds of general formula XL may be prepared from the compounds of general formula XXXIX by arylsulphonylation with an arylsulphonyl chloride, e.g. p-toluenesulphonyl chloride or benzenesulphonyl chloride, in an inert organic solvent, e.g. methylene chloride, in the presence of a base, e.g. pyridine or a tertiary amine, at room temperature. The bromides of general formula XLI are prepared by reaction of the compounds of general formula XL with lithium bromide in N,N-dimethylformamide at room temperature. The fluorides of general formula XLII are prepared by reaction of the compounds of general formula XLI with 1,4,7,10,13,16-hexaoxacyclooctadecane and potassium fluoride in acetonitrile. The compounds of general formula XLII may also be prepared by reaction of the alcohols of general formula XXXIX with sulphur tetrafluoride.

It is known that alkyl chlorides, alkyl bromides or alkyl iodides are unstable under basic conditions, but that alkyl fluorides are stable under those conditions. Compounds of general formula XXXVIII may be prepared from the compounds of general formula XLII by means heretofore mentioned for the conversion of the compounds of general formula XXXV to those of general formula XXIV.

The prostaglandin analogues of general formula VII, wherein $R^1$ represents a hydrogen atom and the other symbols are as hereinbefore defined, obtained by the hereinbefore described processes can be converted by methods known per se into salts or alkyl esters having from 1 to 12 carbon atoms in the alkyl radical.

The salts may be prepared from the compounds of general formula VII, wherein $R^1$ represents a hydrogen atom, by methods known per se, for example by reaction of stoichiometric quantities of acids of general formula VII and the appropriate base, e.g. an alkali metal hydroxide or carbonate, ammonium hydroxide, ammonia or an amine, in a suitable solvent. The salts may be isolated by concentration of the solution, or if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the prostaglandins of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

Alkyl esters of the prostaglandins of general formula VII can be obtained by reaction of the acids with (i) diazoalkane compounds, e.g. diazomethane, (ii) alcohols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our British Pat. Nos. 1,362,956 and 1,364,125).

The prostaglandin analogues of general formula VII may, if desired, be converted by methods know per se into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrate. $\alpha$, $\beta$ or $\gamma$-Cyclodextrins or mixtures thereof may be used in the preparation of the cyclodextrin clathrates. Conversion into their cyclodextrin clathrates serves to increase the stability of the prostaglandin compounds.

The prostaglandin analogues of general formula VII and their cyclodextrin clathrates and, when $R^1$ represents a hydrogen atom, non-toxic salts possess the valuable pharmacological properties typical of the prostaglandins in a selective fashion, in particular hypotensive activity, inhibitory activity on blood platelet aggregation, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis and myocardial infarction, in the treatment of gastric ulceration, and more especially in the termination of pregnancy and induction of labour in pregnant female mammals and in the treatment of impaired fertility, and in the control of oestrus, contraception and menstrual regulation in female mammals. For example, in standard laboratory tests (i) by intravenous administration to the allobarbital-anaesthetized dog, 9-oxo-11$\alpha$,15R-dihydroxy-16,16-propano-20-chloroprost-trans-13-enoic acid methyl ester produces falls in blood pressure of 26 mm Hg and 46 mm Hg lasting 10 and 14 minutes at the doses of 2 and 4 $\mu$g/kg animal body weight, respectively; (ii) in stress ulceration of rats [produced according to the method of Takagi and Okabe—Jap. J. Pharmac, 18, 9–18(1968) by soaking rats in a water bath at 19° C. for 6 hours], 9-oxo-11$\alpha$,15R-dihydroxy-16,16-propano-20-bromoprost-trans-13-enoic acid methyl ester produces 36.2% and 79.1% inhibitions of stress ulceration by oral administration at the doses of 200 and 500 $\mu$g/kg animal body weight, respectively, and (iii) 9-oxo-11$\alpha$,15R-dihydroxy-16,16-propano-20-chloroprost-trans-13-enoic acid methyl ester, 9-oxo-11$\alpha$,15R-dihydroxy-16,16-propano-20-bromoprost-trans-13-enoic acid methyl ester and 9-oxo-11$\alpha$,15R-dihydroxy-16,16-propano-20-fluoroprost-trans-13-enoic acid methyl ester stimulate uterine contraction in the pregnant female rat when administered intravenously on the 20th day of gestation at the doses of 0.2, 0.2 and 0.1–0.2 $\mu$g/kg animal body weight, respectively. The prostaglandin compounds of the present invention and their cyclodextrin clathrates and non-toxic salts possess relatively low potencies in inducing diarrhoea in comparison with their potencies in respect of the valuable properties hereinbefore described. For example the doses by oral administration of 9-oxo-11$\alpha$,15R-dihydroxy-16,16-propano-20-chloroprost-trans-13-enoic acid methyl ester, 9-oxo-11$\alpha$,15R-dihydroxy-16,16-propano-20-bromoprost-trans-13-enoic acid methyl ester and 9-oxo-11$\alpha$,15R-dihydroxy-16,16-propano-20-fluoroprost-trans-13-enoic acid methyl ester required to produce diarrhoea in 50% of mice so treated are 0.74, 1.8 and 1–2 mg/kg animal body weight, respectively.

In the compounds of general formula VII preferably $R^1$ represents a hydrogen atom or a methyl group, preferably A represents a grouping of formula VIIIB, in which the hydroxy group attached to the carbon atom in the 11-position is in $\alpha$-configuration, preferably W represents ethylene, preferably X represents ethylene, preferably Y represents trans-vinylene, preferably B represents the tetramethylene group and preferably Z represents a fluorine, chlorine or bromine atom.

Preferred compounds of the invention are methyl 9-oxo-11α,15R-dihydroxy-16,16-propano-20-iodoprost-trans-13-enoate, methyl 9α,11α,15R-trihydroxy-16,16-propano-20-fluoroprosta-cis-5,trans-13-dienoate,
methyl 9α,11α,15R-trihydroxy-16,16-propano-20-chloroprosta-cis-5,trans-13-dienoate, methyl 9α,11α,15R-trihydroxy-16,16-propano-20-bromoprosta-cis-5,trans-13-dienoate, methyl 9α,11α,15R-trihydroxy-16,16-propano-20-iodoprosta-cis-5,trans-13-dienoate,
methyl 9-oxo-11α,15R-dihydroxy-16,16-propano-20-fluoroprosta-cis-5,trans-13-dienoate, methyl 9-oxo-11α,15R-dihydroxy-16,16-propano-20-chloroprosta-cis-5,trans-13-dienoate, methyl 9-oxo-11α,15R-dihydroxy-16,16-propano-20-bromoprosta-cis-5,trans-13-dienoate,
methyl 9-oxo-11α,15R-dihydroxy-16,16-propano-20-iodoprosta-cis-5,trans-13-dienoate, methyl 9-oxo-11α,15R-dihydroxy-16,16-propano-20-fluoroprosta-trans-2,trans-13-dienoate, methyl 9-oxo-11α,15R-dihydroxy-16,16-propano-20-chloroprosta-trans-2,trans-13-dienoate, methyl 9-oxo-11α,15R-dihydroxy-16,16-propano-20-bromoprosta-trans-2,trans-13-dienoate and methyl 9-oxo-11α,15R-dihydroxy-16,16-propano-20-iodoprosta-trans-2,trans-13-dienoate.

Especially preferred compounds of the invention are methyl 9-oxo-11α,15R-dihydroxy-16,16-propano-20-fluoroprost-trans-13-enoate, methyl 9-oxo-11α,15R-dihydroxy-16,16-propano-20-chloroprost-trans-13-enoate and methyl 9-oxo-11α,15R-dihydroxy-16,16-propano-20-bromoprost-trans-13-enoate.

The compounds of general formulae X, XI, XII and XIIC are new and as such they, and the processes for their preparation hereinbefore described, constitute features of the present invention.

The following Reference Examples and Examples illustrate the process of the present invention and products thereof. In the Examples 'IR', 'NMR', 'Mass', 'b.p' and 'TLC' represent respectively 'Infrared absorption spectrum', 'Nuclear magnetic resonance spectrum', 'Mass spectrum', 'boiling point' and 'Thin layer chromatography'. Solvent ratios, e.g. for chromatographic separations, are by volume.

REFERENCE EXAMPLE 1

4-Chloro-1-tetrahydropyran-2'-yloxybutane

A solution of 64 g of 4-chlorobutan-1-ol (0.59 mol), a catalytic amount of hydrogen chloride and 59.5 g of 2,3-dihydropyran in 180 ml of methylene chloride was stirred for 30 minutes at room temperature. The reaction was then quenched by addition of pyridine. The reaction mixture was concentrated to give an oily residue which was diluted with chloroform, washed with water, dried over anhydrous sodium sulphate, concentrated and distilled under reduced pressure to give 110 g of the title compound (b.p. 67°–68° C./1 mm Hg) having the following physical characteristics:

IR (liquid film): $\nu=1080, 1030$ cm$^{-1}$;

NMR (CDCl$_3$ solution): $\delta=4.56$ (1H, m), 4.00–3.30 (6H, m).

REFERENCE EXAMPLE 2

6-Tetrahydropyran-2'-yloxy-2,2-propanohexanoic acid

To a solution of 38.5 g of diisopropylamine (0.381 mol) in 184 ml of tetrahydrofuran was added dropwise 224 ml of a 1.6 M solution of n-butyllithium (0.381 mol) in n-hexane at −30° C. and then 17.3 g of cyclobutanecarboxylic acid (0.173 mol) was added dropwise to the reaction mixture at the same temperature and the reaction mixture was stirred at −10° C. for 40 minutes. To the reaction mixture thus obtained was added 40.0 g of 4-chloro-1-tetrahydropyran-2'-yloxybutane (0.208 mol; prepared as described in Reference Example 1) and the reaction mixture was stirred for 24 hours. The reaction mixture was then poured into ice-water, the organic layer was removed and the aqueous layer was acidified to pH 2 with 2 N hydrochloric acid and extracted with diethyl ether. The extract was washed with water, dried over anhydrous sodium sulphate and concentrated under reduced pressure to give 42 g of the title compound as an oil having the following physical characteristics:

IR (liquid film): $\nu=3600-2300, 1710, 1080, 1030$ cm$^{-1}$;

NMR (CDCl$_3$ solution): $\delta=9.80$ (1H, broad s), 4.60 (1H, m), 4.00–3.25 (4H, m).

REFERENCE EXAMPLE 3

Methyl 6-hydroxy-2,2-propanohexanoate

To 37 g of 6-tetrahydropyran-2'-yloxy-2,2-propanohexanoic acid (prepared as described in Reference Example 2) was added 250 ml of a 6 M solution of hydrogen chloride in methanol at room temperature and the reaction mixture was stirred at 40° to 50° C. for 1 hour and concentrated under reduced pressure to give 32 g of an oily substance. The oily substance was distilled under reduced pressure to give 22.3 g of the title compound having the following physical characteristics:

b.p.: 92°–96° C./1 mm Hg;

IR (liquid film): $\nu=3450, 1720$ cm$^{-1}$;

NMR (CDCl$_3$ solution): $\delta=3.68$ (3H, s), 3.61 (2H, t, J=6.5 Hz);

Mass: m/e=186 (M$^+$), 168, 114.

REFERENCE EXAMPLE 4

Methyl 6-tetrahydropyran-2'-yloxy-2,2-propanohexanoate

A catalytic amount of p-toluenesulphonic acid and 5.2 g of 2,3-dihydropyran were added to a solution of 10 g of methyl 6-hydroxy-2,2-propanohexanoate (prepared as described in Reference Example 3) in 120 ml of methylene chloride and the reaction mixture was stirred at room temperature for 30 minutes. A few drops of pyridine were then added to the reaction mixture. The reaction mixture was washed with water, dried over anhydrous sodium sulphate and concentrated under reduced pressure to give 15.0 g of the title compound as an oil having the following physical characteristics:

IR (liquid film): $\nu=1730, 1080, 1030$ cm$^{-1}$;

NMR (CDCl$_3$ solution): $\delta=4.55$ (1H, m), 3.67 (3H, s), 4.00–3.20 (4H, m);

Mass: m/e=270 (M$^+$), 252, 238, 169.

REFERENCE EXAMPLE 5

Dimethyl 2-oxo-3,3-propano-7-tetrahydropyran-2'-yloxyheptyl-phosphonate

To a solution of 16.6 g of dimethyl methylphosphonate in 100 ml of tetrahydrofuran was added dropwise 84 ml of a 1.6 M solution of n-butyllithium in n-hexane at −70° C. under an atmosphere of nitrogen. The reaction mixture was stirred for 15 minutes at the same temperature and a solution of 15.0 g of methyl 6-tetrahydropyran-2'-yloxy-2,2-propanohexanoate (prepared as described in Reference Example 4) in 100 ml of tetrahydrofuran was added to the reaction mixture at −70° C. After stirring for 50 minutes at −70° C. and then for 2 hours at room temperature, the reaction mixture was neutralized with 8.1 g of acetic acid and then concentrated under reduced pressure. The residue was dissolved in water and extracted three times with diethyl ether. The extract was dried over anhydrous sodium sulphate and concentrated under reduced pressure to give 20.5 g of the title compound as an oil having the following physical characteristics:

IR (liquid film): $\nu = 1710, 1240, 1040$ cm$^{-1}$;

NMR (CDCl$_3$ solution): $\delta = 4.53$ (1H, m), 3.86 (3H, s), 3.75 (3H, s), 3.90–3.20 (4H, m), 3.05 (2H, d, J=21.5 Hz);

Mass: m/e=362 (M$^+$), 333, 307, 206.

REFERENCE EXAMPLE 6

1S-2-oxa-3-oxo-6R-(3-oxo-4,4-propano-8-tetrahydropyran-2'-yloxy-oct-trans-1-enyl)-7R-p-phenylbenzoyloxy-cis-bicyclo[3,3,0]octane To a solution of 0.473 g of chlorine in 8.5 ml of carbon tetrachloride was added at −10° C. a solution of 0.826 g of thioanisole in 10 ml of methylene chloride under an atmosphere of argon. A white precipitate appeared immediately after addition of the thioanisole. The reaction mixture was cooled to −25° C. and a solution of 1.23 g of 1S-2-oxa-3-oxo-6R-hydroxymethyl-7R-p-phenylbenzoyloxy-cis-bicyclo[3,3,0]octane [prepared as described by E. J. Corey et al., J. Amer. Chem. Soc., 93, 1491(1971)] in 22 ml of methylene chloride was added dropwise. Stirring was continued for 90 minutes at −25° C., and then a solution of 1.32 g of triethylamine in 10 ml of methylene chloride was added dropwise to the reaction mixture. Cooling was discontinued, and after 5 minutes ice-cold 1% (w/v) aqueous hydrochloric acid was added. The organic layer was dried over anhydrous magnesium sulphate and concentrated under reduced pressure to obtain the crude aldehyde, 1S-2-oxa-3-oxo-6R-formyl-7R-p-phenylbenzoyloxy-cis-bicyclo[3,3,0]octane, as a white solid which was washed twice with cold n-pentane and then used immediately in the next step.

To a suspension of 0.0936 g of sodium hydride in 38 ml of 1,2-dimethoxyethane was added a solution of 1.4 g of dimethyl 2-oxo-3,3-propano-7-tetrahydropyran-2'-yloxyheptylphosphonate (prepared as described in Reference Example 5) in 18 ml of 1,2-dimethoxyethane under an atmosphere of argon. The reaction mixture was stirred at room temperature until no further hydrogen was evolved. The reaction mixture was cooled to from 3° to 5° C., and a solution of the crude aldehyde (obtained as described above) in 20 ml of 1,2-dimethoxyethane was added and the reaction mixture was stirred at room temperature for 40 minutes. After addition of 234 mg of acetic acid to the reaction mixture, the solvent was removed under reduced pressure and at a temperature <30° C. The residue was dissolved in water and extracted with ethyl acetate. The organic layer was washed with water, dried over anhydrous magnesium sulphate, and concentrated under reduced pressure to give an oily residue. The oily residue was treated with diisopropyl ether to give 1.61 g of the amorphous title compound having the following physical characteristics:

IR (KBr tablet): $\nu = 1765, 1710, 1690, 1615$ cm$^{-1}$;

NMR (CDCl$_3$ solution): $\delta = 8.1$–7.4 (9H, m), 6.80 (1H, q, J=15.5, 7 Hz), 6.38 (1H, d, J=15.5 Hz), 5.34 (1H, m), 5.12 (1H, m), 4.50 (1H, m);

Mass: m/e=586 (M$^+$), 502, 484, 430.

REFERENCE EXAMPLE 7

1S-2-oxa-3-oxo-6R-(3R-hydroxy-4,4-propano-8-tetrahydropyran-2'-yloxy-oct-trans-1-enyl)-7R-p-phenylbenzoyloxy-cis-bicyclo[3,3,0]octane To a solution of 11.3 g of 1S-2-oxa-3-oxo-6R-(3-oxo-4,4-propano-8-tetrahydropyran-2'-yloxy-oct-trans-1-enyl)-7R-p-phenylbenzoyloxy-cis-bicyclo[3,3,0]octane (prepared as described in Reference Example 6) in a mixture of 140 ml of absolute methanol and 70 ml of anhydrous tetrahydrofuran was gradually added 2.9 g of sodium borohydride at −30° C. After stirring for 15 minutes, the reaction mixture was quenched by addition of 5.1 ml of acetic acid, and concentrated. The residue was dissolved in water, the mixture was extracted with chloroform and the extract was washed with a saturated aqueous solution of sodium bicarbonate and then with water, dried over anhydrous magnesium sulphate and concentrated under reduced pressure to yield 12.5 g of an oily product. The oily product was purified by column chromatography on silica gel using a mixture of benzene and methyl ethyl ketone (85:15) as eluant. The following fractions were collected:
(a) desired 3R-alcohol, 4.7 g;
(b) a mixture of 3R- and 3S-alcohol, 2.3 g; and
(c) 3S-alcohol, 4.1 g.
(1) 3R-alcohol has the following physical characteristics:

IR (CHCl$_3$ solution): $\nu = 3600$–3400, 1770, 1720, 1610, 1280, 1120, 1080, 1030, 980, 910, 860 cm$^{-1}$;

NMR (CDCl$_3$ solution): $\delta = 8.13$–7.34 (9H, m), 5.90–5.54 (2H, m), 5.42–4.95 (2H, m), 4.54 (1H, m), 4.12–3.96 (1H, m);

Mass: m/e=504 (M$^+$-84), 486, 461, 377, 376;

Optical rotation: $[\alpha]_D^{25} = -69.4°$ (c=2.32, CHCl$_3$ solution).

(2) 3S-alcohol has the following physical characteristics:

IR (CHCl$_3$ solution): $\nu = 3600$–3400, 1770, 1710, 1610, 1280, 1120, 1080, 1030, 970, 900, 860 cm$^{-1}$;

NMR (CDCl$_3$ solution): $\delta = 8.18$–7.24 (9H, m) 5.80–5.32 (2H, m), 5.43–4.94 (2H, m) 4.54 (1H, m), 4.10–3.95 (1H, m);

Mass: m/e=486 (M$^+$-102), 468, 461, 377, 376;

Optical rotation: $[\alpha]_D^{23} = -86.5°$ (c=1.95, CHCl$_3$ solution).

REFERENCE EXAMPLE 8

1S-2-oxa-3-oxo-6R-(3R-hydroxy-4,4-propano-8-tetrahydropyran-2'-yloxy-oct-trans-1-enyl)-7R-hydroxy-cis-bicyclo[3,3,0]octane To a solution of 4.6 g of 1S-2-oxa-3-oxo-6R-(3R-hydroxy-4,4-propano-8-tetrahydropyran-2'-yloxy-oct-trans-1-enyl)-7R-p-phenylbenzoyloxy-cis-bicyclo[3,3,0]octane (prepared as described in Reference Example 7) in 40 ml of absolute methanol was added 1.1 g of finely powdered anhydrous potassium carbonate and the reaction mixture was stirred at room temperature for 1.5 hours and then cooled in an ice bath. After addition of 15.8 ml of 1 N hydrochloric acid, the reaction mixture was extracted three times with chloroform. The extract was washed with a saturated aqueous solution of sodium bicarbonate, dried over anhydrous sodium sulphate, and concentrated under reduced pressure to yield an oily product. The oily product was purified by column chromatography on silica gel using a mixture of chloroform and methanol (20:1) as eluant to give 3.2 g of the title compound having the following physical characteristics:

IR (CHCl$_3$ solution): $\nu$=3600–3400, 1770, 1170, 1080, 1030, 980 cm$^{-1}$;

NMR (CDCl$_3$ solution): $\delta$=5.82–5.32 (2H, m), 4.88 (1H, m), 4.54 (1H, m);

Mass: m/e=324 (M$^+$-84), 306, 295, 288.

REFERENCE EXAMPLE 9

1S-2-oxa-3-oxo-6R-(3R,8-bis-tetrahydropyran-2'-yloxy-4,4-propanooct-trans-1-enyl)-7R-tetrahydropyran-2'-yloxy-cis-bicyclo[3,3,0]octane To a solution of 3.2 g of 1S-2-oxa-3-oxo-6R-(3R-hydroxy-4,4-propano-8-tetrahydropyran-2'-yloxy-oct-trans-1-enyl)-7R-hydroxy-cis-bicyclo[3,3,0]octane (prepared as described in Reference Example 8) in 30 ml of methylene chloride were added 1.4 g of 2,3-dihydropyran and a catalytic amount of p-toluenesulphonic acid, and the reaction mixture was stirred for 15 minutes at room temperature. The reaction was quenched by addition of a few drops of pyridine and the reaction mixture was diluted with chloroform, washed with water, dried over anhydrous sodium sulphate and concentrated under reduced pressure to yield 4.5 g of the title compound. The crude product was used without purification in Reference Example 10 described hereinafter and has the following physical characteristic:

Mass: m/e=372 (M$^+$-204), 306, 288.

REFERENCE EXAMPLE 10

1S-2-oxa-3$\xi$-hydroxy-6R-(3R,8-bis-tetrahydropyran-2'-yloxy-4,4-propanooct-trans-1-enyl)-7R-tetrahydropyran-2'-yloxy-cis-bicyclo[3,3,0]octane To a stirred cold solution (−70° C.) of 4.5 g of the crude 1S-2-oxa-3-oxo-6R-(3R,8-bis-tetrahydropyran-2'-yloxy-4,4-propanooct-trans-1-enyl)-7R-tetrahydropyran-2'-yloxy-cis-bicyclo[3,3,0]octane (prepared as described in Reference Example 9) in 60 ml of anhydrous toluene was added dropwise 16.1 ml of a 25%(w/v) solution of diisobutylaluminium hydride in n-hexane under an atmosphere of argon. The reaction mixture was stirred for 20 minutes at −70° C. and then quenched by addition of 22 ml of methanol, allowed to warm to room temperature, stirred for 15 minutes and diluted with diethyl ether. The organic layer was washed with a saturated aqueous solution of sodium bitartrate, dried over anhydrous magnesium sulphate and concentrated under reduced pressure to give 4.5 g of the title compound as an oil. The compound was used immediately, without purification, in Example 1 described hereinafter.

EXAMPLE 1

9$\alpha$-hydroxy-11$\alpha$,15R,20-tri-tetrahydropyran-2'-yloxy-16,16-propanoprosta-cis-5,trans-13-dienoic acid Sodium methylsulphinylmethylide was prepared as follows: A mixture of 4485 mg of sodium hydride (65.1% content) and 60 ml of anhydrous dimethyl sulphoxide was stirred at 60° C. until gas evolution ceased (ca. 2 hours). After cooling to room temperature, the solution was ready for use.

To a solution of 16.8 g of dried (4-carboxybutyl)-triphenyl-phosphonium bromide in 30 ml of anhydrous dimethyl sulphoxide was added 43.6 ml of the dimethyl sulphoxide solution of sodium methylsulphinylmethylide (prepared as described above) with stirring to give a solution of an ylide to which, after a further 5 minutes stirring, a solution of 4.5 g of 1S-2-oxa-3$\xi$-hydroxy-6R-(3R,8-bis-tetrahydropyran-2'-yloxy-4,4-propanooct-trans-1-enyl)-7R-tetrahydropyran-2'-yloxy-cis-bicyclo[3,3,0]octane (prepared as described in Reference Example 10) in 15 ml of anhydrous dimethyl sulphoxide was added. The reaction mixture was stirred at 25° C. for 2 hours, at 50° C. for an additional 30 minutes, and then quenched with ice-water. The reaction mixture was diluted with a mixture of ethyl acetate and diethyl ether (1:1), the aqueous layer was separated and the organic layer was extracted with an aqueous solution of potassium carbonate. The two aqueous layers thus obtained were combined, acidified to pH 2–3 with 1 N hydrochloric acid and extracted with a mixture of n-pentane and diethyl ether (1:1). The acidic extracts were dried over anhydrous magnesium sulphate and concentrated under reduced pressure to give 4.0 g of an oily product. The oily product was purified by column chromatography on silica gel using a mixture of chloroform and methanol (20:1) as eluant to give 3.1 g of the title compound having the following physical characteristics:

IR (CHCl$_3$ solution): $\nu$=3600–2300, 1715, 1140, 1120, 1080, 1030, 980, 910, 870 cm$^{-1}$;

NMR (CDCl$_3$ solution): $\delta$=5.65–5.15 (6H, m), 4.80–4.52 (3H, m), 4.20–3.30 (11H, m);

Mass: m/e=476 (M$^+$-186), 458, 410, 392, 374, 356.

EXAMPLE 2

Methyl 9$\alpha$-hydroxy-11$\alpha$,15R,20-tri-tetrahydropyran-2'-yloxy-16,16-propanoprosta-cis-5,trans-13-dienate A solution of diazomethane in diethyl ether was added to a solution of 2.65 g of 9$\alpha$-hydroxy-11$\alpha$,15R,20-tri-tetrahydropyran-2'-yloxy-16,16-propanoprosta-cis-5,trans-13-dienoic acid (prepared as described in Example 1) in 30 ml of methanol until the yellow colour did not vanish. After stirring for a few minutes at room temperature the reaction mixture was concentrated under reduced pressure to give an oily product. The oily product was purified by column chromatography on silica gel using a mixture of benzene and ethyl acetate (8:1) as eluant to give 2.24 g of the title compound having the following physical characteristics:

IR (CHCl$_3$ solution): $\nu$=3600–3400, 1730, 1440, 1360, 1140, 1120, 1080, 1030, 980, 910, 870 cm$^{-1}$;

NMR (CDCl$_3$ solution): $\delta$=5.63–5.26 (4H, m), 4.78–4.50 (3H, m), 3.65 (3H, s), 4.30–3.30 (11H, m);

Mass: m/e=490 (M$^+$-186), 472, 406, 388.

EXAMPLE 3

Methyl 9$\alpha$-hydroxy-11$\alpha$,15R,20-tri-tetrahydropyran-2'-yloxy-16,16-propanoprost-trans-13-enoate A solution of 385 mg of methyl 9$\alpha$-hydroxy-11$\alpha$,15R,20-tri-tetrahydropyran-2'-yloxy-16,16-propanoprosta-cis-5,trans-13-dienoate (prepared as described in Example 2) in 10 ml of methanol was subjected to catalytic hydrogenation in the presence of 5%(w/w) palladium on carbon as catalyst. Hydrogenation was carried out at room temperature and atmospheric pressure until the starting material could not be detected by thin layer chromatography on a silica gel plate pre-treated with silver nitrate [a mixture of chloroform and methanol (10:1) was used as developing solvent]. After the reaction the catalyst was filtered off and the resulting filtrate was concentrated under reduced pressure to give 389 mg of the title compound having the following physical characteristics:

IR (CHCl$_3$ solution): $\nu$=3600–3400, 1730, 1440, 1360, 1140, 1120, 1080, 1030, 980, 910, 870 cm$^{-1}$;

NMR (CDCl$_3$ solution): $\delta$=5.63–5.30 (2H, m), 4.78–4.50 (3H, m), 4.30–3.30 (11H, m), 3.65 (3H, m);

Mass: m/e=492 (M$^+$−186), 474, 408, 390.

EXAMPLE 4

Methyl 9-oxo-11α,15R,20-tri-tetrahydropyran-2'-yloxy-16,16-propanoprost-trans-13-enoate A solution of 5.7 g of manganese sulphate in 28 ml of water was treated with 1.36 ml of concentrated sulphuric acid followed by 1.3 g of chromium trioxide at 0° C. to obtain a solution of oxidizing agent ready for use.

To a solution of 380 mg of methyl 9α-hydroxy-11α,15R,20-tri-tetrahydropyran-2'-yloxy-16,16-propanoprost-trans-13-enoate (prepared as described in Example 3) in 5 ml of diethyl ether was added the previously prepared oxidizing agent at 0° C. After stirring for 2.5 hours at 0° C. the reaction mixture was diluted with diethyl ether. The organic layer was washed with a saturated aqueous solution of sodium chloride, dried over anhydrous magnesium sulphate and concentrated under reduced pressure to yield an oily product. The product was purified by column chromatography on silica gel using diethyl ether as eluant to give 361 mg of the title compound having the following physical characteristics:

IR (CHCl$_3$ solution): $\nu$=1740, 1440, 1360, 1130, 1080, 1030, 970, 900, 860 cm$^{-1}$;

NMR (CDCl$_3$ solution): $\delta$=5.75–5.45 (2H, m), 4.80–4.50 (3H, m), 3.65 (3H, s), 4.05–3.25 (11H, m);

Mass: m/e=490 (M$^+$−186), 472, 406, 388.

EXAMPLE 5

Methyl 9-oxo-11α,15R,20-trihydroxy-16,16-propanoprost-trans-13-enoate

To a solution of 350 mg of methyl 9-oxo-11α,15R,20-tri-tetrahydropyran-2'-yloxy-16,16-propanoprost-trans-13-enoate (prepared as described in Example 4) in 1 ml of tetrahydrofuran was added 3 ml of a 65% (v/v) aqueous solution of acetic acid. The reaction mixture was stirred for 2.5 hours at 37° C. and concentrated under reduced pressure to give an oily product containing acetic acid which was removed azeotropically with toluene under reduced pressure. The residue was purified by column chromatography on silica gel using a mixture of chloroform and methanol (20:1) as eluant to give 166 mg of the title compound having the following physical characteristics:

IR (CHCl$_3$ solution): $\nu$=3600–3400, 1740 cm$^{-1}$;

NMR (CDCl$_3$ solution): $\delta$=5.90–5.45 (2H, m), 4.15–3.95 (2H, m), 3.66 (3H, s), 3.75–3.65 (2H, m);

Mass: m/e=394 (M$^+$−18), 376.

EXAMPLE 6

Methyl 9-oxo-11α,15R-dihydroxy-16,16-propano-20-(p-toluenesulphonyloxy)prost-trans-13-enoate To a solution of 150 mg of methyl 9-oxo-11α,15R,20-trihydroxy-16,16-propanoprost-trans-13-enoate (prepared as described in Example 5) in 8 ml of methylene chloride were added 33.5 mg of pyridine and 81 mg of p-toluenesulphonyl chloride at 0° C. The reaction mixture was stirred at 0° C. for 4 hours and then at room temperature for 24 hours. The reaction mixture was purified by column chromatography on silica gel using a mixture of chloroform and methanol (20:1) as eluant to give 166 mg of the oily title compound having the following physical characteristics:

IR (CHCl$_3$ solution): $\nu$=3600–3400, 1740, 1600, 1360, 1180, 1100, 970, 930 cm$^{-1}$;

NMR (CDCl$_3$ solution): $\delta$=7.78 (2H, d, J=8 Hz), 7.34 (2H, d, J=8 Hz), 5.85–5.46 (2H, m) 4.15–3.90 (4H, m), 3.65 (3H, s), 2.45 (3H, s);

Mass: m/e=560 (M$^+$−18), 398, 380.

EXAMPLE 7

Methyl 9-oxo-11α,15R-dihydroxy-16,16-propano-20-chloro-prost-trans-13-enoate

To a solution of 166 mg of methyl 9-oxo-11α,15R-dihydroxy-16,16-propano-20-(p-toluenesulphonyloxy)-prost-trans-13-enoate (prepared as described in Example 6) in 5 ml of N,N-dimethylformamide was added 24.4 mg of lithium chloride. The reaction mixture was stirred at room temperature for 24 hours and concentrated under reduced pressure. The residue was diluted with ethyl acetate and the mixture was washed with an aqueous solution of sodium chloride, dried over magnesium sulphate and concentrated under reduced pressure to give an oily product. The product was purified by column chromatography on silica gel using a mixture of chloroform and methanol (20:1) as eluant to give 92 mg of the title compound having the following physical characteristics:

IR (CHCl$_3$ solution): $\nu$=3600–3400, 1740 cm$^{-1}$;

NMR (CDCl$_3$ solution): $\delta$=5.94–5.50 (2H, m), 4.15–3.90 (2H, m), 3.66 (3H,s), 3.56 (2H, t, J=7.0 Hz);

Mass: m/e=424 (M$^+$−18), 406, 374.

EXAMPLE 8

Methyl 9-oxo-11α,15R-dihydroxy-16,16-propano-20-bromo-prost-trans-13-enoate

By proceeding as described in Example 7, but using 140 mg of methyl 9-oxo-11α,15R-dihydroxy-16,16-propano-20-(p-toluenesulphonyloxy)-prost-trans-13-enoate (prepared as described in Example 6) and 48 mg of lithium bromide, there was obtained 103 mg of the title compound having the following physical characteristics:

IR (CHCl$_3$ solution): $\nu$=3600–3400, 1740 cm$^{-1}$;

NMR (CDCl$_3$ solution): $\delta$=5.88–5.45 (2H, m), 4.21–3.85 (2H, m), 3.66 (3H, s), 3.45 (2H, t, J=6.5 Hz);

Mass: m/e=468 (M$^+$−18), 450, 418.

REFERENCE EXAMPLE 11

Methyl 6-(p-toluenesulphonyloxy)-2,2-propanohexanoate

To a solution of 40 g of methyl 6-hydroxy-2,2-propanohexanoate (prepared as described in Reference Example 3) in 240 ml of pyridine was added 45.2 g of p-toluenesulphonyl chloride at −5° C. and the reaction mixture was stirred at −5° C. for 5 hours. The reaction mixture was poured into 500 ml of ice-water and extracted three times with 250 ml of diethyl ether. The organic layer was washed with water, 2 N hydrochloric acid and water, dried over anhydrous magnesium sulphate and concentrated under reduced pressure to give 62 g of the title compound having the following physical characteristics:

NMR (CDCl$_3$ solution): δ=7.78 (2H, d, J=8.5 Hz), 7.35 (2H, d, J=8.5 Hz), 4.01 (2H, t, J=6.5 Hz), 3.66 (3H, s), 2.45 (3H, s).

REFERENCE EXAMPLE 12

Methyl 6-bromo-2,2-propanohexanoate

To a solution of 62 g of methyl 6-(p-toluenesulphonyloxy)-2,2-propanohexanoate (prepared as described in Reference Example 11) in 300 ml of acetone was added 47 g of lithium bromide at −5° C. The reaction mixture was stirred at −5° C. for 30 minutes and then at room temperature for 24 hours and concentrated under reduced pressure. The residue was diluted with 250 ml of water and extracted with diethyl ether. The extract was washed with water, dried over anhydrous magnesium sulphate, concentrated and distilled under reduced pressure to give 40 g of the title compound having the following physical characteristics:

b.p.: 82°-85° C./0.7 mm Hg;

NMR (CDCl$_3$ solution): δ=3.68 (3H, s), 3.39 (2H, t, J=6.5 Hz).

REFERENCE EXAMPLE 13

Methyl 6-fluoro-2,2-propanohexanoate (i). A mixture of 5.0 g of methyl 6-bromo-2,2-propanohexanoate (prepared as described in Reference Example 12), 10.0 ml of sulphur tetrafluoride, 5 g of sodium fluoride and 20 ml of chloroform was reacted in a sealed tube at 25° C. for 17 hours and then at 80° C. for 1.5 hours. The reaction mixture was poured into a saturated aqueous solution of sodium bicarbonate and extracted with chloroform. The extract was washed with water, dried over anhydrous sodium sulphate, concentrated and distilled under reduced pressure to give an oily product. The oily product was further distilled carefully using a spinning-band column under reduced pressure to give 1.0 g of the title compound having the following physical characteristics:

b.p.: 60°-63° C./2 mm Hg;

IR (liquid film): ν=1730, 1340 cm$^{-1}$;

NMR (CDCl$_3$ solution): δ=4.39 (2H, d,t, J$_{H-F}$=47 Hz, J$_{H-H}$=6 Hz), 3.66 (3H, s).

(ii). To a solution of 5.8 g of 1,4,7,10,13,16-hexaoxacyclooctadecane in 80 ml of acetonitrile was added 18.7 g of potassium fluoride and the reaction mixture was stirred at room temperature for 40 minutes. To the reaction mixture thus obtained was added 40 g of methyl 6-bromo-2,2-propanohexanoate (prepared as described in Reference Example 12). The reaction mixture was refluxed for 18 days and then concentrated under reduced pressure. Water was added to the residue and the mixture was extracted with diethyl ether. The extract was washed with water, dried over anhydrous magnesium sulphate and concentrated under reduced pressure to give 30 g of an oily product. The oily product was distilled carefully under reduced pressure using a spinning-band column to give 16.3 g of the title compound having the aforementioned physical characteristics.

REFERENCE EXAMPLE 14

Dimethyl 2-oxo-3,3-propano-7-fluoroheptylphosphonate

By proceeding as described in Reference Example 5 but replacing the methyl 6-tetrahydropyran-2'-yloxy-2,2-propanohexanoate by 8.0 g of methyl 6-fluoro-2,2-propanohexanoate (prepared as described in Reference Example 13) dissolved in 45 ml of tetrahydrofuran and utilizing 12.7 g of dimethyl methylphosphonate and 65.3 ml of a 1.6 M solution of n-butyllithium in n-hexane, there was obtained 14.7 g of an oily product. The oily product was distilled under reduced pressure to give 9.8 g of the title compound having the following physical characteristics:

b.p.: 139°-149° C./1 mm Hg;

IR (liquid film): ν=1710, 1250, 1030 cm$^{-1}$;

NMR (CDCl$_3$ solution): δ=4.42 (2H, d,t, J$_{H-F}$=47 Hz, J$_{H-H}$=6 Hz), 3.80 (6H, d, J=11.5 Hz), 3.06 (2H, d, J=21.5 Hz);

Mass: m/e=280 (M$^+$), 262, 252, 219, 206.

REFERENCE EXAMPLE 15

1S-2-Oxa-3-oxo-6R-(3-oxo-4,4-propano-8-fluorooct-trans-1-enyl)-7R-p-phenylbenzyloxy-cis-bicyclo[3,3,0]octane By proceeding as described in Reference Example 6 but replacing the dimethyl 2-oxo-3,3-propano-7-tetrahydropyran-2'-xyloxyheptylphosphonate by 5.852 g of dimethyl 2-oxo-3,3-propano-7-fluoroheptylphosphonate (prepared as described in Rerence Example 14) dissolved in 90 ml of 1,2-dimethoxyethane, there was obtained 8.0 g of the title compound having the following physical characteristics:

m.p.: 138°-140° C. (recrystallized from diisopropyl ether);

IR (KBr tablet): ν=1765, 1710, 1680, 1620, 1270, 1050, 890, 850, cm$^{-1}$;

NMR (CDCl$_3$ solution): δ=8.20–7.20 (9H, m), 6.80 (1H, q, J=15.5, 7 Hz), 6.38 (1H, d, J=15.5 Hz), 5.45–5.20 (1H, m), 5.20–4.95 (1H, m), 4.30 (2H, d,t, J$_{H-F}$=47 Hz, J$_{H-H}$=6 Hz);

Mass: m/e=504 (M$^+$), 430, 352, 306, 198.

REFERENCE EXAMPLE 16

1S-2-Oxa-3-oxo-6R-(3R-hydroxy-4,4-propano-8-fluorooct-trans-1-enyl)-7R-p-phenylbenzoyloxy-cis-bicyclo[3,3,0]octane By proceeding as described in Reference Example 7 but replacing the 1S-2-oxa-3-oxo-6R-(3-oxo-4,4-propano-8-tetrahydropyran-2'-yloxyoct-trans-1-enyl)-7R-p-phenylbenzoyloxy-cis-bicyclo[3,3,0]octane by 10.3 g of 1S-2-oxa-3-oxo-6R-(3-oxo-4,4-propano-8-fluorooct-trans-1-enyl)-7R-p-phenylbenzoyloxy-cis-bicyclo[3,3,0]octane (prepared as described in Reference Example 15) dissolved in a mixture of 180 ml of absolute methanol and 90 ml of anhydrous tetrahydrofuran and utilizing 3.1 g of sodium borohydride, there were obtained 5.44 g of the title compound, 1.42 g of a mixture of 3R- and 3S-alcohol and 3.00 g of 3S-alcohol. The title compound and the 3S-alcohol showed the following physical characteristics:

3R-alcohol;

m.p.: 123°–124° C. (recrystallized from diisopropyl ether);

IR (KBr tablet): $\nu=3600–3400$, 1770, 1690, 1610, 1290 cm$^{-1}$;

NMR (CDCl$_3$ solution): $\delta=8.15–7.30$ (9H, m), 5.74–5.57 (2H, m), 5.38–4.93 (2H, m), 4.37 (2H, d,t, $J_{H-F}=47$ Hz, $J_{H-H}=6$ Hz), 4.12–3.96 (1H, m);

Mass: m/e=506 (M$^+$), 488 (M$^+$ −18), 378, 308, 290.

3S-alcohol;

IR (CHCl$_3$ solution): $\nu=3600–3400$, 1770, 1715, 1610, 1280 cm$^{-1}$;

NMR (CDCl$_3$ solution): $\delta=8.12–7.30$ (9H, m), 5.74–5.57 (2H, m), 5.38–5.14 (1H, m), 5.14–4.95 (1H, m), 4.38 (2H, d,t, $J_{H-F}=47$ Hz, $J_{H-H}=6$ Hz), 4.06–3.95 (1H, m);

Mass: m/e 506 (M$^+$), 488 (M$^+$ −18), 178, 308, 290.

REFERENCE EXAMPLE 17

1S-2-Oxa-3-oxo-6R-(3R-hydroxy-4,4-propano-8-fluorooct-trans-1-enyl)-7R-hydroxy-cis-bicyclo[3,3,0]octane By proceeding as described in Reference Example 8 but replacing the 1S-2-oxa-3-oxo-6R-(3R-hydroxy-4,4-propano-8-tetrahydropyran-2′-yloxy-oct-trans-1-enyl)-7R-p-phenylbenzoyloxy-cis-bicyclo[3,3,0]octane by 2.53 g of 1S-2-oxa-3-oxo-6R-(3R-hydroxy-4,4-propano-8-fluorooct-trans-1-enyl)-7R-p-phenylbenzoyloxy-cis-bicyclo[3,3,0]octane (prepared as described in Reference Example 16) dissolved in 45 ml of absolute methanol and utilizing 0.69 g of anhydrous potassium carbonate, there was obtained 1.65 g of the title compound having the following physical characteristics:

IR (CHCl$_3$ solution): $\nu=3600–3400$, 1770, 1170, 980 cm$^{-1}$;

NMR (CDCl$_3$ solution): $\delta=5.80–5.33$ (2H, m), 5.00–4.76 (1H, m), 4.76–4.57 (1H, m) 4.30–4.10 (1H, m), 4.06–3.80 (2H, m);

Mass: m/e=326 (M$^+$), 308 (M$^+$ −18), 209, 198.

REFERENCE EXAMPLE 18

1S-2-Oxa-3-oxo-6R-(3R-tetrahydropyran-2′-yloxy-4,4-propano-8-fluorooct-trans-1-enyl)-7R-tetrahydropyran-2′-yloxy-cis-bicyclo[3,3,0]octane By proceeding as described in Reference Example 9 but replacing the 1S-2-oxa-3-oxo-6R-(3R-hydroxy-4,4-propano-8-tetrahydropyran-2′-yloxyoct-trans-1-enyl)-7R-hydroxy-cis-bicyclo[3,3,0]octane by 1.598 g of 1S-2-oxa-3-oxo-6R-(3R-hydroxy-4,4-propano-8-fluorooct-trans-1-enyl)-7R-hydroxy-cis-bicyclo[3,3,0]octane (prepared as described in Reference Example 17) dissolved in 20 ml of methylene chloride and utilizing 1.0 g of 2,3-dihydropyran, there was obtained 2.548 g of the title compound. The crude product was used without purification in Reference Example 19 described hereinafter and has the following physical characteristic:

Mass: m/e=326 (M$^+$ −268), 308 (M$^+$ −296), 281 (M$^+$ −311).

REFERENCE EXAMPLE 19

1S-2-Oxa-3ξ-hydroxy-6R-(3R-tetrahydropyran-2′-yloxy-4,4-propano-8-fluorooct-trans-1-enyl)-7R-tetrahydropyran-2′-yloxy-cis-bicyclo[3,3,0]octane By proceeding as described in Reference Example 10 but replacing the 1S-2-oxa-3-oxo-6R-(3R,8-bis-tetrahydropyran-2′-yloxy-4,4-propanooct-trans-1-enyl)-7R-tetrahydropyran-2′-yloxy-cis-bicyclo[3,3,0]octane by 2.548 g of 1S-2-oxa-3-oxo-6R-(3R-tetrahydropyran-2′-yloxy-4,4-propano-8-fluorooct-trans-1-enyl)-7R-tetrahydropyran-2′-yloxy-cis-bicyclo[3,3,0]octane (prepared as described in Reference Example 18) dissolved in 40 ml of anhydrous toluene and utilizing 10.4 ml of a 25%(w/v) solution of diisobutylaluminium hydride in n-hexane, there was obtained 2.60 g of the title compound as an oil. The compound was used immediately, without purification, in Example 9 described hereinafter.

EXAMPLE 9

9α-Hydroxy-11α,15R-bis-tetrahydropyran-2′-yloxy-16,16-propano-20-fluoroprosta-cis-5,trans-13-dienoic acid By proceeding as described in Example 1 but replacing the 1S-2-oxa-3ξ-hydroxy-6R-(3R,8-bis-tetrahydropyran-2′-yloxy-4,4-propanooct-trans-1-enyl)-7R-tetrahydropyran-2′-yloxy-cis-bicyclo[3,3,0]octane by 2.60 g of 1S-2-oxa-3ξ-hydroxy-6R-(3R-tetrahydropyran-2′-yloxy-4,4-propano-8-fluorooct-trans-1-enyl)-b 7R-tetrahydropyran-2′-yloxy-cis-bicyclo[3,3,0]octane (prepared as described in Reference Example 19) dissolved in 10 ml of anhydrous dimethyl sulphoxide, there was obtained 2.672 g of the title compound having the following physical characteristics:

IR (CHCl$_3$ solution): $\nu=3600–3400$, 1715, 1125, 1080, 1030, 980, 910, 870 cm$^{-1}$;

NMR (CDCl$_3$ solution): $\delta=5.70–5.25$ (6H, m), 4.80–4.55 (3H, m), 4.25–3.65 (6H, m), 3.65–3.30 (2H, m);

Mass: m/e=394 (M$^+$ −186), 376 (M$^+$ −204).

EXAMPLE 10

Methyl 9α-hydroxy-11α,15R-bis-tetrahydropyran-2′-yloxy-16,16-propano-20-fluoroprosta-cis-5,trans-13-dienoate By proceeding as described in Example 2 but replacing the 9α-hydroxy-11α,15R,20-tri-tetrahydropyran-2′-yloxy-16,16-propanoprosta-cis-5,trans-13-dienoic acid by 2.6 g of 9α-hydroxy-11α,15R-bis-tetrahydropyran-2′-yloxy-16,16-propano-20-fluoroprosta-cis-5,trans-13-dienoic acid (prepared as described in Example 9) dissolved in 30 ml of methanol, there was obtained 2.3 g of the title compound having the following physical characteristic:

Mass: m/e=492 (M$^+$ −102), 418, 390, 336.

EXAMPLE 11

Methyl 9α-hydroxy-11α,15R-bis-tetrahydropyran-2′-yloxy-16,16-propano-20-fluoroprost-trans-13-enoate By proceeding as described in Example 3 but replacing the methyl 9α-hydroxy-11α,15R,20-tritetrahydropyran-2′-yloxy-16,16-propanoprosta-cis-5,trans-13-dienoate by 407 mg of methyl 9α-hydroxy-11α,15R-bis-tetrahydropyran-2′-yloxy-16,16-propano-20-fluoroprosta-cis-5,trans-13-dienoate (prepared as described in Example 10) dissolved in 10 ml of methanol and utilizing 100 mg of 5%(w/w) palladium on carbon, there was obtained 423 mg of the title compound having the following physical characteristics:

IR (CHCl$_3$ solution): $\nu$=3600–3400, 1730, 1440, 1140, 1120, 1080, 1030, 980, 910, 870 cm$^{-1}$;

NMR (CDCl$_3$ solution): $\delta$=5.73–5.20 (2H, m), 4.75–4.57 (3H, m), 4.30–3.73 (6H, m), 3.65 (3H, s), 3.57–3.32 (2H, m);

Mass m/e=410 (M$^+$−186), 392 (M$^+$−204), 338, 299.

EXAMPLE 12

Methyl 9-oxo-11$\alpha$,15R-bis-tetrahydropyran-2'-yloxy-16,16-propano-20-fluoroprost-trans-13-enoate By proceeding as described in Example 4 but replacing the methyl 9$\alpha$-hydroxy-11$\alpha$,15R,20-tritetrahydropyran-2'-yloxy-16,16-propanoprost-trans-13-enoate by 390 mg of methyl 9$\alpha$-hydroxy-11$\alpha$,15R-bis-tetrahydropyran-2'-yloxy-16,16-propano-20-fluoroprost-trans-13-enoate (prepared as described in Example 11) dissolved in 5 ml of diethyl ether and utilizing 10 ml of oxidizing agent, prepared as described in Example 4, there was obtained 378 mg of the title compound having the following physical characteristics:

IR (CHCl$_3$ solution): $\nu$=1740, 1440, 1130, 1080, 1040, 1030, 980, 905, 875 cm$^{-1}$;

NMR (CDCl$_3$ solution): $\delta$=5.72–5.30 (2H, m), 4.80–4.55 (3H, m), 4.26–3.70 (6H, m), 3.64 (3H, s), 3.60–3.35 (2H, m);

Mass: m/e=408 (M$^+$−186), 390 (M$^+$−204), 337, 297.

EXAMPLE 13

Methyl 9-oxo-11$\alpha$,15R-dihydroxy-16,16-propano-20-fluoroprost-trans-13-enoate By proceeding as described in Example 5 but replacing the methyl 9-oxo-11$\alpha$,15R,20-tritetrahydropyran-2'-yloxy-16,16-propanoprost-trans-13-enoate by 363 mg of methyl 9-oxo-11$\alpha$,15R-bis-tetrahydropyran-2'-yloxy-16,16-propano-20-fluoroprost-trans-13-enoate (prepared as described in Example 12), there was obtained 255 mg of the title compound having the following physical characteristics:

IR (CHCl$_3$ solution): $\nu$=3600–3400, 1730, 1430, 1230, 1070, 970 cm$^{-1}$;

NMR (CDCl$_3$ solution): $\delta$=5.75–5.57 (2H, m), 4.44 (2H, d,t, $J_{H\text{-}F}$=47 Hz, $J_{H\text{-}H}$=6 Hz), 4.13–3.94 (2H, m), 3.65 (3H, s);

Mass: m/e=408 (M$^+$), 390 (M$^+$−18), 297, 280, 279.

The present invention includes within its scope pharmaceutical compositions which comprise at least one prostaglandin analogue of general formula VII or a cyclodextrin clathrate thereof or, when R$^1$ represents a hydrogen atom, a non-toxic salt thereof, together with a pharmaceutical carrier or coating. In clinical practice the compounds of general formula VII and cyclodextrin clathrates thereof and, when R$^1$ represents a hydrogen atom, non-toxic salts thereof will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention for oral administration also include capsules of absorbable material such as gelatin containing one or more of the active substances with or without the addition of diluents or excipients.

Solid compositions for rectal administration include suppositories formulated in manner known per se and containing one or more of the active compounds.

Solid compositions for vaginal administration include pessaries formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses per person are generally between 0.001 and 50 mg by oral, intravaginal, intrauterine, intravenous, intramuscular or extraovular administration in the termination of pregnancy and induction of labour, in treatment of impaired fertility and in contraception and menstrual regulation. In domestic female mammals such as cows, mares, sows, ewes and bitches, the doses are generally between 0.001 and 50 mg/animal by intramuscular, subcutaneous, intrauterine, intravaginal and intravenous administration for the control and synchronisation of oestrus, treatment of impaired fertility and the induction of abortion and labour.

The following Examples illustrate pharmaceutical compositions according to the invention.

EXAMPLE 14

Methyl 9-oxo-11$\alpha$,15R-dihydroxy-16,16-propano-20-bromoprost-trans-13-enoate (2 mg) was dissolved in ethanol (10 ml), mixed with mannitol (18.5 g), sieved through a 30-mesh sieve, dried at 30° C. for 90 minutes and again sieved through a 30-mesh sieve. Aerosil (microfine silica; 200 mg) was added and the powder obtained was machine filled into one hundred No. 2 hard gelatin capsules to give capsules each containing 20 μg of methyl 9-oxo-11α,15R-dihydroxy-16,16-propano-20-bromoprost-trans-13-enoate which after swallowing of the capsule is released into the stomach.

EXAMPLE 15

Methyl 9-oxo-11α,15R-dihydroxy-16,16-propano-20-fluoroprost-trans-13-enoate (5 mg) was dissolved in ethanol (25 ml). The solution was then sterilized by passage through a bacteria-retaining filter and placed in 0.1 ml portions in 1 ml ampoules, to give 20 μg of methyl 9-oxo-11α,15R-dihydroxy-16,16-propano-20-fluoroprost-trans-13 enoate per ampoule. The ampoules were sealed. The contents of an ampoule diluted to a suitable volume, e.g. 1 ml, with physiological saline solution, gave a solution ready for administration by injection.

We claim:

1. A prostaglandin analogue of the general formula:

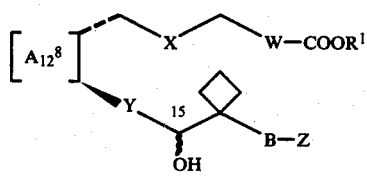

wherein A represents a grouping of the formula:

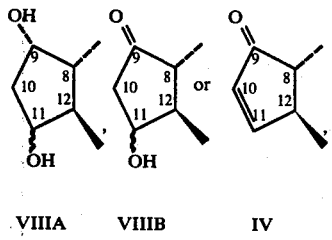

B represents a straight- or branched-chain alkylene group containing from 1 to 7 carbon atoms, X represents ethylene or cis-vinylene, Y represents ethylene or trans-vinylene, W represents ethylene or trans-vinylene, Z represents a halogen atom, and $R^1$ represents a hydrogen atom or a straight- or branched-chain alkyl group containing from 1 to 12 carbon atoms and cyclodextrin clathrates of such acids and esters and, when $R^1$ represents a hydrogen atom, non-toxic salts thereof.

2. A prostaglandin analogue according to claim 1, wherein $R^1$ represents a hydrogen atom or a methyl group.

3. A prostaglandin analogue according to claim 1, wherein A represents a grouping of general formula VIIIA or VIIIB in which the hydroxy group depicted in formulae VIIIA and VIIIB in α- or β-configuration is attached to the 11-position carbon atom in α-configuration.

4. A prostaglandin analogue according to claim 1, wherein A represents a grouping of general formula VIIIB in which the hydroxy group attached to the carbon atom in the 11-position is in α-configuration.

5. A prostaglandin analogue according to claim 1, wherein W represents ethylene.

6. A prostaglandin analogue according to claim 1, wherein X represents ethylene.

7. A prostaglandin analogue according to claim 1, wherein Y represents trans-vinylene.

8. A prostaglandin analogue according to claim 1, wherein B represents the tetramethylene group.

9. A prostaglandin analogue according to claim 1, wherein Z represents a fluorine, chlorine or bromine atom.

10. A prostaglandin analogue according to claim 1, wherein the hydroxy radical attached to the carbon atom in the 15-position of general formula VII depicted in claim 1 is in α-configuration.

11. A prostaglandin analogue according to claim 1 which is methyl 9-oxo-11α,15R-dihydroxy-16,16-propano-20-chloroprost-trans-13-enoate.

12. A prostaglandin analogue according to claim 1 which is methyl 9-oxo-11α,15R-dihydroxy-16,16-propano-20-bromoprost-trans-13-enoate.

13. A prostaglandin analogue according to claim 1 which is methyl 9-oxo-11α,15R-dihydroxy-16,16-propano-20-fluoroprost-trans-13-enoate.

14. A non-toxic salt of a prostaglandin analogue as claimed in claim 1, wherein $R^1$ in general formula VII depicted in claim 1 represents a hydrogen atom.

15. A cyclodextrin clathrate of a prostaglandin analogue as claimed in claim 1.

16. Pharmaceutical compositions useful for the contraception and menstrual regulation in females and in the termination of pregnancy and the induction of labor in pregnant females which comprise, as active ingredient, at least one prostaglandin analogue as claimed in claim 1 or a cyclodextrin clathrate thereof or, when $R^1$ in general formula VII depicted in claim 20 represents a hydrogen atom, a non-toxic salt thereof, in association with a pharmaceutical carrier or coating.

* * * * *